United States Patent [19]
Berzofsky et al.

[11] Patent Number: 5,820,865
[45] Date of Patent: Oct. 13, 1998

[54] METHOD TO INDUCE CYTOTOXIC T LYMPHOCYTES SPECIFIC FOR A BROAD ARRAY OF HIV-1 ISOLATES USING HYBRID SYNTHETIC PEPTIDES

[75] Inventors: Jay A. Berzofsky, Bethesda, Md.; Hidemi Takahashi, Tokyo, Japan; Ronald N. Germain, Potomac, Md.

[73] Assignee: The United States of America as represented by the Department of Health and Human Services, Washington, D.C.

[21] Appl. No.: 760,530

[22] Filed: Sep. 18, 1991

Related U.S. Application Data

[63] Continuation-in-part of Ser. No. 148,692, Jan. 26, 1988, abandoned.

[51] Int. Cl.$^6$ .................................................... A61K 39/21
[52] U.S. Cl. ................................... 424/188.1; 424/208.1; 530/326; 530/327
[58] Field of Search ............................. 435/172.3, 235.1; 530/328, 324–327; 424/89, 188.1, 184.1, 187.1, 208.1; 935/65; 930/221

[56] References Cited

U.S. PATENT DOCUMENTS 5,562,905  10/1996  Kenealy et al. ...................... 424/188.1

FOREIGN PATENT DOCUMENTS

| 0273716 | 7/1988 | European Pat. Off. |
| WO86/02383 | 4/1986 | WIPO |
| WO8702775 | 5/1987 | WIPO |
| WO87/07616 | 12/1987 | WIPO |

OTHER PUBLICATIONS

H. Takahashi et al. Proc. Natl. Acad Sci. USA 85:3105 (1988).
H. Takahashi et al, Science 246:118 (1989).
H. Takahashi et al, J.Exp.Med. 170:2023 (1989).
H. Takahashi et al, Nature 334:873 (1990).
Takahashi, H. et al., *Science*, 246:118–121, 1989.
Neuroth, A.R. et al. "Confronting the Hypervariability of an Immunodominant Epitope Eliciting Virus Neutralizing Antibodies from the Envelope Glycoprotein of the Human Immunodeficiency Virus type 1(HIV 1)". Mol. Immun. vol. 27, No. 6 pp. 539–549, 1990.
Takahashi, Hidemi et al. "A Single Amino Acid Interchange Yields Reciprocal CTL Specificities of HIV–1 gp160", Science 10/6/1989. vol. 246 pp. 118–121.
Klinman, Dennis M. et al "Sequential Immunizations with rgp 120;from Independent Isolates of HIV–1 Induce the Preferential Expansion of Broadly Crossreactive B Cells." J. Exp. Med. vol. 173, Apr. 91 pp. 881–887.
Nari, Peter et al "Clonal Dominance of the Neutralizing Response to the HIV–1 V–3 Epitope: Evidence for Original Antigenic Sin during Vaccination and Infection on Animal, Including Humans" Vaccines 91 pp. 881–887. Cold Spring Harbor lab.
Weinhold, Kent et al "Human T–cell Clones Define Distinct Epitopes Within the V–3 Region of HIV–1 gp120". V Int. Conf. on AIDS, Montreal Jun. 4–9 1989. 545.
Fultz, P.N. et al "Infection of Non–human Primates with Human and Simian Immunodeficiency Viruses." *AIDS Vaccine Research and Clinical Trials*. Putney SD& Bolognesi DP editors. NY, 1990. pp. 339–349. Abstract.
Hileman MR. "Conclusions: In Pursuit of an AIDS Virus Vaccine" Abstract. Immunol. Ser. 44:605–620. 1989.
Eichberg, J.W. Experience with 13 HIV Efficiency trials on Chimpanzees. Int Conf. on AIDS Jun. 20–23,1990, 6 (1) p. 204. Abstract # Th.A.338.
Fauci, AS et al. "Development and evaluation of a Vaccine for HIV infection" Ann Intern. Med. Mar. 1, 1989. 110 (5) pp. 373–385.
Vacolio et al. Sequences Outside A Minimal Immundominant Site Exert Negative Effects on Recognition By Staphylococcal.
Nuclease–Specific T–Cell Clones *J. of Immunol.* vol. 143, No. 9, Nov. 1, 1989, pp. 2814–2819.
Kumar et al. "Amino–acid variations at a single residue in an autoimmune peptide profoundly affect its properties: T–cell activation . . . allergic encephalomyelitis" *PNAS* 87, Feb. 1990 pp. 1337–1341.
LaRosa et al. "Conserved Sequence & Structural Elements in the HIV–1 Principal Neutralizing Determinant" *Science* V.249 24 Aug. 1990, pp. 932–935.
Rusche et al. "Antibodies that inhibit fusion of human immunodeficiency virus–infected cells bind a 24–amino acid sequence of the viral envelope, gp120".
*PNAS* vol. 85, May 1988, pp. 3198–3202.
Javaherian et al. "Principal neutralizing domain of the human immunodeficiency type 1 envelope protein".
*PNAS* vol. 86, Sep. 1989, pp. 6768–6772.

*Primary Examiner*—Jeffrey Stucker
*Attorney, Agent, or Firm*—Fish & Richardson P.C.

[57] ABSTRACT

The instant invention describes the synthesis of short peptides, corresponding to the amino acid residues of the V3 loop of the gp16O envelope glycoprotein of HIV-1 numbered 315 to 329 by Ratner (Ratner, L. et al., *Nature* 313, 277 (1985)) in the strain IIIB, wherein the residue corresponding to number 325 in HIV-1 IIIB is substituted by the homologous residue from another clinical isolate or strain. The invention further describes the use of said peptides in pharmaceutical compositions and an immunization protocol which elicits cytotoxic T cells reactive to a broad range of isolates of HIV-1.

8 Claims, 10 Drawing Sheets

METHOD TO INDUCE CYTOTOXIC T LYMPHOCYTES SPECIFIC FOR A BROAD ARRAY OF HIV-1 ISOLATES USING HYBRID SYNTHETIC PEPTIDES

This application is a Continuation-In-Part Of U.S. Pat. application Ser. No. 07/148,692, filed on Jan. 26, 1988 now abandoned.

FIELD OF THE INVENTION

The invention is directed to a series of synthetic peptides useful as vaccines for the prophylaxis or immunotherapy of HIV-1 virus infection. The invention is further directed to pharmaceutical compositions and an immunization protocol utilizing the synthetic peptides to produce cytotoxic T-lymphocytes with cross-reactivity to a broad range of clinical isolates of HIV-1.

BACKGROUND OF THE INVENTION

Scientific publications referred to in this application are hereby incorporated by reference.

The envelope glycoprotein gp160 has been used in numerous prototype vaccine preparations designed for prophylaxis against or immunotherapy of infection by HIV-1 or its close simian lentivirus relatives (Berman, P. W. et al., *Nature* 345, 622 (1990); Zagury, D. et al., *Nature* 332, 728 (1988).; Clerici, M., et al., *Eur. J. Immunol.* 21, 1345 (1991); Redfield, R. R. et al., *N. Engl. J. Med.* 324, 1677 (1991)). Studies in man and mouse have revealed a small region of this protein, called the V3 loop, between cysteine residues 303 and 338, that evokes the major neutralizing antibodies to the virus (Palker, T. J., et al, *Proc. Natl. Acad. Sci. U.S.A.* 85, 1932 (1988); Rusche, J. R., et al., *Proc. Natl. Acad. Sci. U.S.A.* 85, 3198 (1988); Goudsmit, J. et al., *Proc. Natl. Acad. Sci. U.S.A.* 85, 4478 (1988)) and stimulates both helper and cytotoxic T cell responses in both mice and humans (Takahashi, H. et al., *Proc. Natl. Acad. Sci. USA* 85, 3105 (1988); Takahashi, H. et al., *J. Exp. Med.* 171, 571 (1990); Clerici, M. et al., *Nature* 339, 383 (1989); Clerici, M. et al., *J. Immunol.* 146, 2214 (1991)). This same region is one of the most variable in sequence among different clonal isolates (Myers, G. et al., *Human retroviruses and AIDS* 1989 (Los Alamos National Laboratory, N. Mex., 1989); LaRosa, G.J. et al., *Science* 249, 932 (1990)), and this variation has been suggested to arise by selection of mutant virus as a result of the intense immune pressure directed against this region of the molecule (Albert, J. et al., *AIDS* 4, 107 (1990); Nara, P. L. et al., *J. Virol.* 64, 3779 (1990); Takahashi, H. et al., *Science* 246, 118 (1989); Takahashi, H. et al., *J. Exp. Med.* 170, 2023 (1989)). Thus, this segment of gp160 is both an attractive candidate for a major component of an AIDS vaccine because of its known antigenic properties, and a problem for the design of useful vaccines because of the extensive diversity in its structure already existing and likely to arise in the future.

Pircher et al. (Pircher, H. et al., *Nature* 346, 629 (1990)) have directly demonstrated that the LCMV virus can escape cytotoxic T lymphocyte (CTL) immune responses by accumulation of point mutations affecting T cell recognition even while preserving MHC molecule binding and display. Because CTL are likely to play a major role in effective immune responses against HIV-1, due to its capacity for direct intercellular transfer, we have examined the response of mice to this region of gp160. Our previous studies revealed the ability of a single residue change in the 315–329 immunodominant determinant, numbered according to the system of Ratner (Ratner, L. et al., *Nature* 313, 277 (1985)), presented by the class I MHC molecule $D^d$ to completely and reciprocally alter recognition by CTL directed against the MN and IIIB forms of this site (Takahashi, H. et al., *Science* 246, 118 (1989)). This naturally occurring variation in T cell epitopes of gp160 might well be explained by the type of immune selection studied by Pircher et al. (Pircher, H. et al., *Nature* 346, 629 (1990)), as this site is seen by human CTL specific for the HIV envelope (Clerici, M. et al., *J. Immunol.* 146, 2214 (1991)) in addition to neutralizing antibodies (Palker, T. J., et al, *Proc. Natl. Acad. Sci. U.S.A.* 85, 1932 (1988); Rusche, J. R., et al., *Proc. Natl. Acad. Sci. U.S.A.* 85, 3198 (1988); Goudsmit, J. et al., *Proc. Natl. Acad. Sci. U.S.A.* 85, 4478 (1988)). Because an effective anti-HIV vaccine strategy must anticipate to the greatest extent possible such potential changes in viral antigenicity, we have examined in detail the specificity of CTL recognition of numerous HIV-1 isolates and describe a method for immunization that generates broadly reactive CTL with an enhanced capacity to respond to a wide array of variant sequences at this critical immunodominant site.

SUMMARY OF THE INVENTION

It is one object of the invention to provide a peptide or group of peptides, useful for the prophylaxis or immunotherapy of HIV-1 infection, which elicits in the immunized subject cytotoxic T lymphocyte activity against a broad range of clinical isolates of HIV-1. It is a further object of the invention to provide for a pharmaceutical composition including at least one of such peptides and to provide for a method of immunization utilizing said pharmaceutical composition to elicit cytotoxic T lymphocyte response to a broad range of clinical isolates of HIV-1 in the immunized subject.

DETAILED DESCRIPTION OF THE INVENTION

Figure 1:
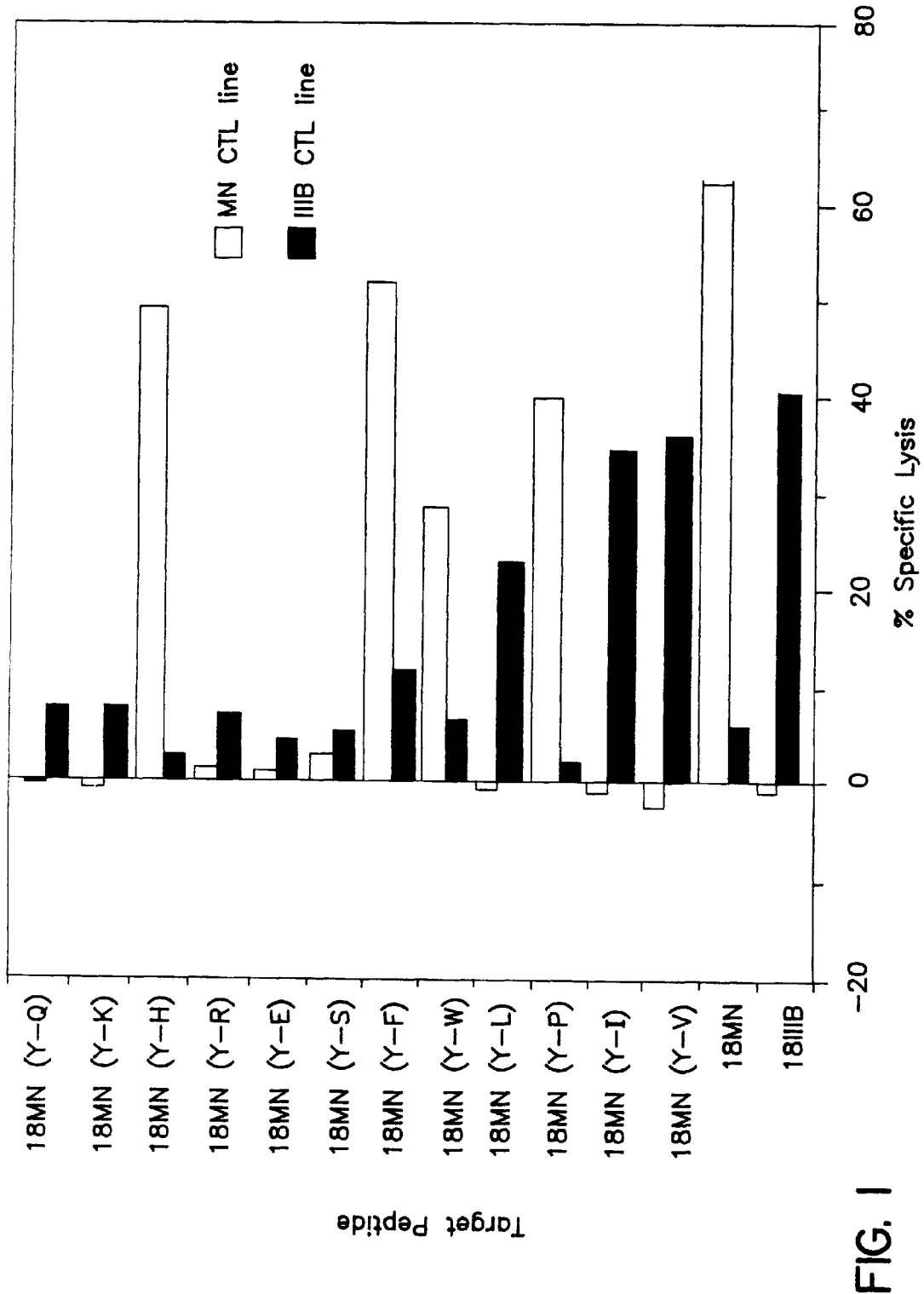
FIG. 1 shows the effect of position 325 substitutions on CTL effector function. CTL-lines specific for either the IIIB (closed bar) or MN (open bar).
Figure 2A:
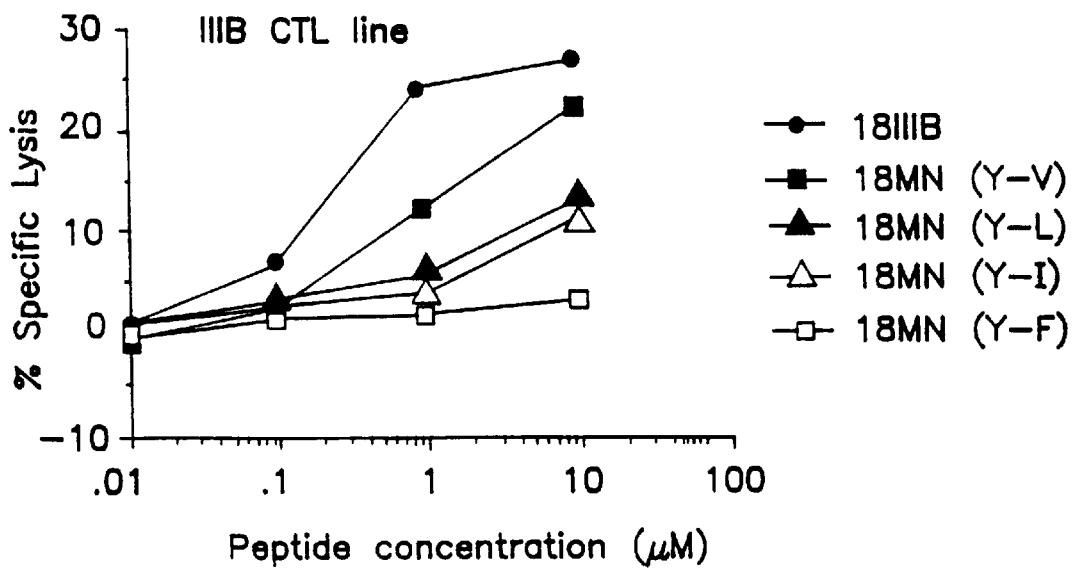
FIG. 2a–b show the relative sensitization potencies of substituted MN peptides. CTL line specific for IIIB (panel A) or MN (panel B) were co-cultured with $^{51}$Cr-labeled BALB/c 3T3 fibroblast targets in the presence of the indicated concentrations of peptides at a 5 to 1 effector to target ratio.
Figure 2B:
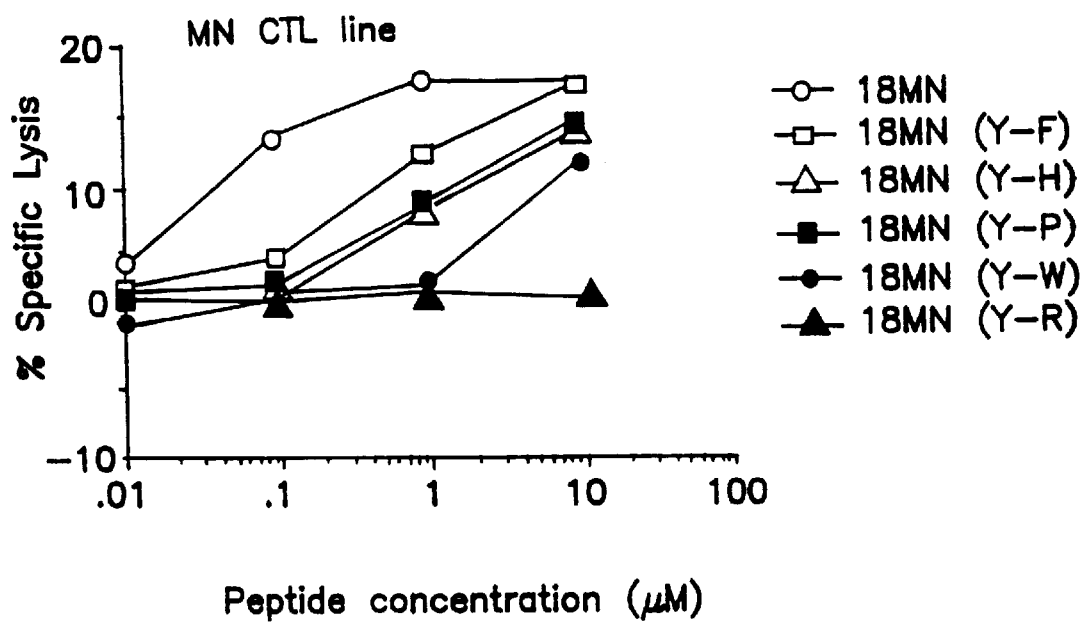

Preferred embodiments of the invention are herein described by means of several examples. These examples are meant to be illustrative, rather than limiting in scope. It is to be understood that slight changes in techniques or materials would be readily obvious to one skilled in the art and such are to be considered within the scope of the present invention.

Example 1

Demonstration of the specificity of induction of cytotoxicity by gp160 and restimulation with homologous synthetic polypeptides of sequences identical to the V3 region amino acids 315 through 329 of natural isolates of HIV-1.

A. Peptide synthesis

A series of peptide analogues of 18 MN are synthesized by solid phase peptide synthesis (J. M. Stewart, J. D. Young, *Solid Phase Peptide Synthesis*, Pierce Chemical Company, Rockford, Ill., 1984), and purified by gel filtration and HPLC.

B. Immunization of mice and T-lymphocyte cytotoxicity assays

Mice are immunized i.v. with $10^7$PFU of recombinant vaccinia viruses, vSC25, vMN or vRF. vSC8 (recombinant vaccinia virus containing the bacterial lacZ gene), vSC-25, vMN, and vRF (recombinant vaccinia viruses expressing the HIV env glycoprotein gp160 of the HIV IIIB, MN, RF isolates, respectively, without other HIV structural or regulatory proteins) have been previously described (Takahashi, H. et al., *Science* 246, 118 (1989); Chakrabarti, S. et al., *Nature* 320, 535 (1986)). Four to 8 weeks later, immune spleen cells ($5 \times 10^6$/ml in 24-well culture plates in complete T-cell medium (Takahashi, H. et al., *J. Exp. Med.* 170, 2023 (1989)) are restimulated for 6 days in vitro with either 0.3 $\mu$M of peptide 18IIIB (RIQRGPGRAFVTIGK) (Seq. I.D. No. 1), representing residues 315 to 329 of the HIV-1 strain IIIB gp160 envelope protein in the numbering system of Ratner et al. (Ratner, L. et al., *Nature*, 313, 277 (1985)), 1 $\mu$M of 18 MN peptide (RIHIGPGRAFYTTKN) (Seq. I.D. No. 2), or 1 $\mu$M 18 RF peptide (SITKGPGRVIYATGQ) (Seq. I.D. No. 3) plus 10% Rat Con-A supernatant-containing medium (Rat T-cell Monoclone) (Collaborative Research, Inc., Bedford, Mass.). After culture for 6 days, cytolytic activity of the restimulated cells is measured as previously described using a 6 hr assay with various $^{51}$Cr-labelled targets. For testing the peptide specificity of CTL, effectors and $^{51}$Cr-labelled targets are mixed with various concentrations of peptide at the beginning of the assay (Takahashi, H. et al., *Proc. Natl. Acad. Sci. USA* 85, 3105 (1988). The variant peptides are synthesized as previously described (Takahashi, H. et al., *Science* 246, 118 (1989); Houghten, R. A. *Proc. Natl. Acad. Sci. USA.* 82, 5131 (1985)). The percent specific $^{51}$Cr release is calculated as 100× [(experimental release—spontaneous release)/(maximum release—spontaneous release)]. Maximum release is determined from supernatants of cells that are lysed by addition of 5% Triton-X 100. Spontaneous release is determined from target cells incubated without added effector cells.

We could elicit from BALB/c (H-$2^d$) mice CTL specific for the peptide SITKGPGRVIYATGQ (Seq. I.D. No.3) (18 RF) the sequence of gp160 from the HIV-1 RF isolate which corresponds to the 315–329 region of gp160 from the IIIB isolate. These CTL did not crossreactively kill targets pulsed with homologous peptides from HIV-1IIIB or HIV-1MN (18IIIB or 18 MN, respectively). Because we had already obtained HIV IIIB and MN envelope-specific CTL lines from BALB/c mice, both restricted by the same $D^d$ class I molecule (Takahashi, H. et al., *Proc. Natl. Acad. Sci. USA* 85, 3105 (1988); Takahashi, H. et al., *Science* 246, 118 (1989)), we had three non-crossreactive, type-specific CTL lines that could kill targets infected with the appropriate gp160-expressing recombinant vaccinia virus as well as targets pulsed with the appropriate peptide. Taking advantage of these CTL lines and a series of synthetic peptides corresponding to the homologous portion of the 14 different HIV isolates shown in Table 1, we analyzed the crossreactivity of each CTL line for each peptide presented by H-$2^d$ cells. The results are summarized in Table 1.

TABLE 1

Crossreactive CTL activity for the homologous portion of the gp160 immunodominant site from different HIV isolates.

| HIV isolates | Sequence 315 | 325 | 329 | IIIB-specific CTL 10 $\mu$M | 1 $\mu$M | MN-specific CTL 10 $\mu$M | 1 $\mu$M | RF-specific CTL 10 $\mu$M | 1 $\mu$M | |
|---|---|---|---|---|---|---|---|---|---|---|
| IIIB | RIQRGPGRAF | V | TIGK | 42.3 | 53.9 | -0.5 | -1.1 | 1.8 | 3.0 | (SEQ. ID 1) |
| MN | RIHIGPGRAF | Y | TTKN | 0.3 | -2.3 | 43.3 | 50.3 | 1.5 | 1.7 | (SEQ. ID 2) |
| RF | SITKGPGRVI | Y | ATGQ | 0.3 | -1.2 | -0.9 | -1.2 | 38.5 | 40.4 | (SEQ. ID 3) |
| SC | SIHIGPGRAF | Y | ATGD | 0.2 | -1.6 | 46.2 | 42.2 | 3.0 | -0.6 | (SEQ. ID 4) |
| WMJ-2 | SLSIGPGRAF | R | TREI | 0.7 | -1.2 | 4.2 | -1.0 | 1.8 | -0.1 | (SEQ. ID 5) |
| Z321 | SISIGPGRAF | F | ATTD | -0.3 | -1.2 | 30.3 | 18.0 | 2.5 | 0.6 | (SEQ. ID 6) |
| SF2 | SIYIGPGRAF | H | TTGR | 0.3 | -0.4 | 25.9 | 13.8 | 1.6 | 0.4 | (SEQ. ID 7) |
| NY5 | GIAIGPGRTL | Y | AREK | -0.4 | -0.7 | 10.2 | 1.0 | 1.4 | -0.2 | (SEQ. ID 8) |
| CDC4 | RVTLGPGRVW | Y | TTGE | 0.0 | -2.0 | 1.0 | -1.5 | 2.6 | -0.2 | (SEQ. ID 9) |
| Z3 | SIRIGPGKVF | T | AKGG | 0.5 | -2.3 | -1.7 | -1.2 | 1.5 | 4.0 | (SEQ. ID 10) |
| MAL | GIHFGPGQAL | Y | TTGI | 0.2 | -2.3 | -1.4 | -2.4 | 2.9 | 1.9 | (SEQ. ID 11) |
| Z6 | STPIGLGQAL | Y | TTRG | -0.6 | -1.7 | -2.1 | -2.7 | -0.7 | -0.9 | (SEQ. ID 12) |
| JY1 | STPIGLGQAL | Y | TTRI | 0.3 | -2.3 | 1.2 | -1.6 | 0.1 | 1.7 | (SEQ. ID 13) |
| ELI | RTPTGLGQSL | Y | TTRS | 0.4 | -0.6 | -0.5 | -2.5 | 2.1 | 0.9 | (SEQ. ID 14) |

*Effector to target ratio is 10:1.

Neither IIIB-specific CTL nor RF-specific CTL crossreactively lyse targets incubated with peptides derived from other HIV isolates. However, MN-specific CTL do crossreactively kill targets incubated with the SC, Z321, SF2, and, weakly, NY5 derived peptides. Thus, significant crosskilling is observed with peptide sequences related to the prevalent MN type.

Example 2

Characterization of the specificity of cytotoxic T lymphocytes using gp160 from a natural HIV-1 isolate and restimulation with chimeric synthetic peptides Previous studies, have demonstrated that the amino acid at position 325 plays a critical role in the specificity of CTL responses to 18IIIB and 18 MN (Takahashi, H. et al., *Science* 246, 118 (1989); Takahashi, H. et al., *J. Exp. Med.* 170, 2023 (1989)). This is consistent with the present observation that MN-specific CTL can strongly recognize targets sensitized with SC, Z321 and SF2 derived peptides, but not those incubated with WMJ-2 or IIIB peptides. These peptides share a common structure of —(I)—GPGRAF—X—(T)—, where X is a variable amino acid at position 325 and the residue present here determines target sensitivity to lysis by a given CTL population. To more systematically examine the effect of changes at this site on the lytic activity of the 18IIIB and 18 MN CTL lines, we synthesized a series of substituted peptides each with a single amino acid substitution at position 325 in 18 MN (J. M. Stewart, J. D. Young, *Solid Phase Peptide Synthesis*, Pierce Chemical Company, Rockford, Ill., 1984). Table II describes the series of peptides synthesized in the experiments of the present example.

Either peptide concentration at the same effector to target ratio (FIG. 2) or effector to target ratio at a constant concentration of peptide is titrated. The results clearly demonstrate that the potency of 18 MN(Y-V) is within ten-fold of that of the original peptide 18IIIB, whereas both 18 MN(Y-I) and 18 MN(Y-L) are 10 to 100 times less active (FIG. 2A). Based on earlier evidence that residue 325 may interact with the T-cell receptor (Takahashi, H. et al., *Science* 246, 118 (1989); Takahashi, H. et al., *J. Exp. Med.* 170, 2023 (1989)), these results suggest that the IIIB-specific CTL T-cell receptor can distinguish fine differences among the three aliphatic amino acids (V, I, L). We also quantitated the activity of the 18 MN, 18 MN(Y-F), 18 MN(Y-H), 18 MN(Y-P), 18 MN(Y-W) peptides using the MN-specific CTL line. As FIG. 2B shows, the 18 MN(Y-F) substitution reduce the ability to sensitize targets approximately 10-fold compared to 18 MN, the 18 MN(Y-H) and 18 MN(Y-P) substitutions reduce the potency nearly 30-fold, and the 18 MN(Y-W) substitution reduce the potency 100-fold. Again, these comparisons indicate that MN-specific CTL T-cell receptors can distinguish the differences among five aromatic or cyclic amino acids (Y, F, H, P, W). Note that for both CTL lines, it is the bulkiest substitution in the relevant chemical category of amino acid that has the least activity, isoleucine in the case of the aliphatic category seen by the IIIB-specific line and tryptophan in the case of the aromatic category seen by the MN-specific line. This observation suggests that the T cell receptors of these CTL have relatively hydrophobic pockets, one set that distinguishes aliphatic from aromatic and the other vice versa, but each of which is too constrained to accept the bulkiest of the side chains in the corresponding category.

TABLE 2

A series of 18MN peptides with a single substitution at position 325.

| Sequence 18MN | 315 R | I | H | I | G | P | G | R | A | F | 325 Y | T | T | K | 329 N | |
|---|---|---|---|---|---|---|---|---|---|---|---|---|---|---|---|---|
| 18MN(Y-V) | R | I | H | I | G | P | G | R | A | F | V | T | T | K | N | (SEQ. ID 15) |
| 18MN(Y-I) | R | I | H | I | G | P | G | R | A | F | I | T | T | K | N | (SEQ. ID 16) |
| 18MN(Y-P) | R | I | H | I | G | P | G | R | A | F | P | T | T | K | N | (SE0. ID 17) |
| 18MN(Y-L) | R | I | H | I | G | P | G | R | A | F | L | T | T | K | N | (SEQ. ID 18) |
| 18MN(Y-W) | R | I | H | I | G | P | G | R | A | F | W | T | T | K | N | (SEQ. ID 19) |
| 18MN(Y-F) | R | I | H | I | G | P | G | R | A | F | F | T | T | K | N | (SEQ. ID 20) |
| 18MN(Y-S) | R | I | H | I | G | P | G | R | A | F | S | T | T | K | N | (SEQ. ID 21) |
| 18MN(Y-E) | R | I | H | I | G | P | G | R | A | F | E | T | T | K | N | (SEQ. ID 22) |
| 18MN(Y-R) | R | I | H | I | G | P | G | R | A | F | R | T | T | K | N | (SEQ. ID 23) |
| 18MN(Y-H) | R | I | H | I | G | P | G | R | A | F | H | T | T | K | N | (SEQ. ID 24) |
| 18MN(Y-K) | R | I | H | I | G | P | G | R | A | F | K | T | T | K | N | (SEQ. ID 25) |
| 18MN(Y-Q) | R | I | H | I | G | P | G | R | A | F | Q | T | T | K | N | (SEQ. ID 26) |

A. Effect of position 325 substitutions on CTL effector function.

CTL-lines specific for either the IIIB (closed bar) or MN (open bar) HIV isolate gp160 are co-cultured during the CTL assay with $^{51}$Cr-labeled BALB/c 3T3 fibroblast targets in the presence of a series of substituted MN peptides at 10 $\mu$M. Effector to target ratio is 5 to 1.

As shown in FIG. 1, the IIIB-specific CTL line can strongly lyse targets sensitized with peptide 18 MN(Y-V) consisting of the 18 MN sequence with 325 Y replaced by V, as we have already reported (Takahashi, H. et al., *Science* 246, 118 (1989)). These CTL can also recognize the substituted peptides 18 MN(Y-I) and 18 MN(Y-L) in which 325(Y) is replaced by either I or L, respectively. The MN-specific CTL line can strongly lyse targets sensitized with 18 MN(Y-F), 18 MN(Y-H), or 18 MN(Y-P) and moderately lyse targets with 18 MN(Y-W), but fails to lyse cells treated with 18 MN(Y-R). These results are compatible with the data in Table 1 that MN-specific CTL can crossreactively kill targets sensitized with Z321 (325(F)) or with SF2 (325(H)), but do not show crossreactivity for targets pulsed with 18WMJ-2 (325(R)). These results confirm and extend the conclusion that the amino acid at position 325 plays a major role in defining the specificity of CTL responses of H-$2^d$ mice to the gp160 315–329 region (Takahashi, H. et al., *Science* 246, 118 (1989); Takahashi, H. et al., *J. Exp. Med.* 170, 2023 (1989)). They also suggest a chemical basis for cross-reactive CTL function, in that IIIB-specific CTL tend to see an aliphatic amino acid at 325 like V, I, or L, whereas MN-specific CTL tend to see an aromatic amino acid like Y, F, H, or W or a ring structure such as P.

B. Comparison of the potency of the crossreactive peptides for the IIIB-specific CTL line CTL line specific for IIIB ( panel A) or MN (panel B) are co-cultured with $^{51}$Cr-labeled BALB/c 3T3 fibroblast targets in the presence of the indicated concentrations of peptides at a 5 to 1 effector to target ratio.

Example 3

Restimulation of the IIIB-gp160 primed immune cells with substituted MN peptides generates broader CTL specificities Highly isolate-specific CTL immunity upon vaccination is unlikely to provide appropriate protection against the range of HIV-1 variants present in the population. To examine whether a broader range of effector CTL specificities are induced by varying the epitopic structure of the antigen during priming and boosting, immune spleen cells from mice primed with recombinant vaccinia virus expressing IIIB gp160 are restimulated with either 18IIIB or several different 18 MN-like peptides substituted at position 325. Immune spleen cells from mice primed with recombinant vaccinia virus vSC25 expressing the IIIB-gp160 gene are restimulated 6 days with either 18IIIB or 18 MN peptides (1

μM) substituted at position 325, plus IL-2. The resulting CTL are assayed on targets incubated with the indicated peptides.

Figure 3A:
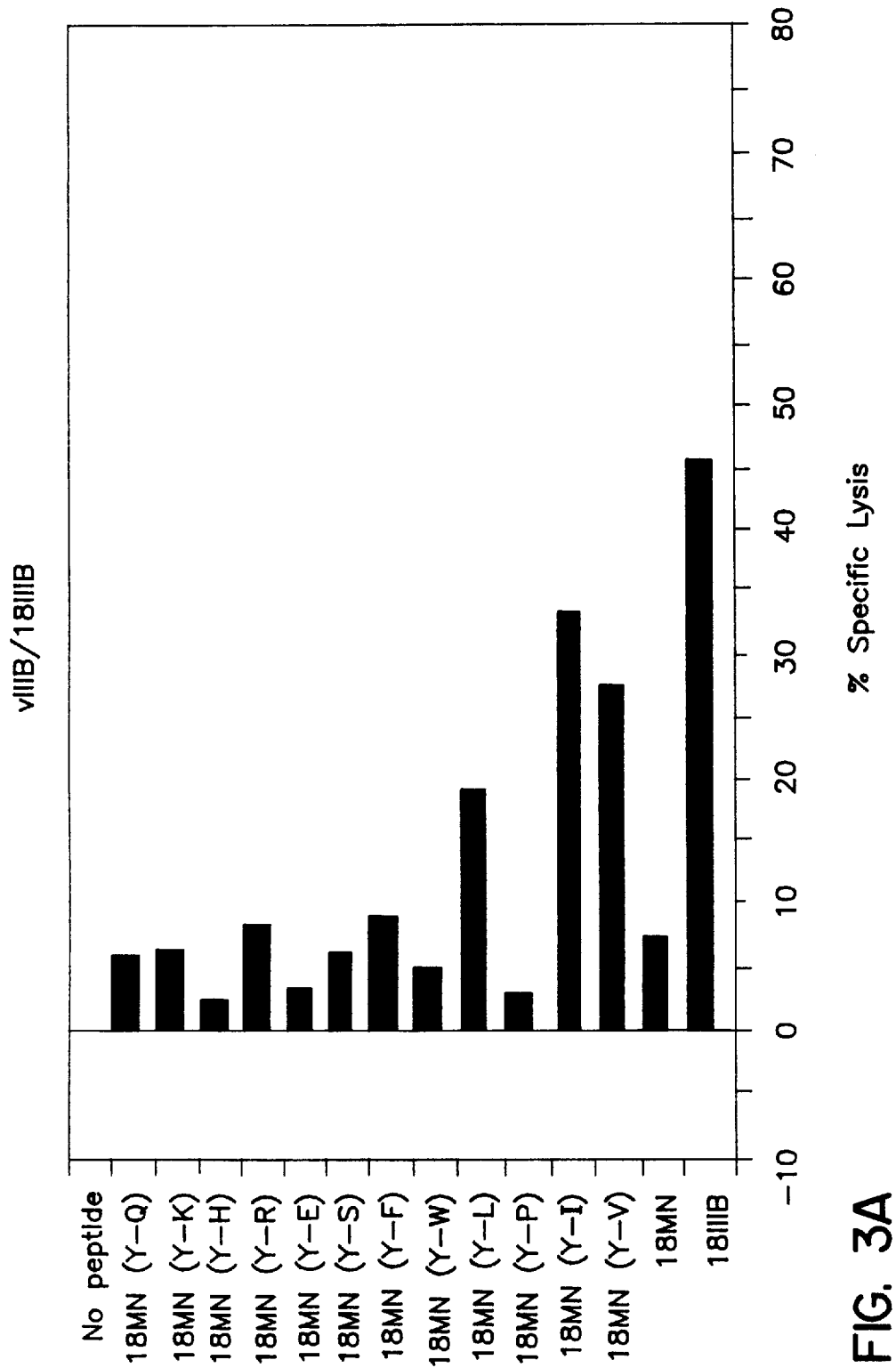
FIG. 3a–h shows restimulation of the IIIB-gp160 primed immune cells with substituted MN peptides. At the top of each panel, a–h, the designation before the slash indicates the recombinant vaccinia virus used for immunization, and that after the slash the peptide used for restimulation in vitro.
Figure 3B:
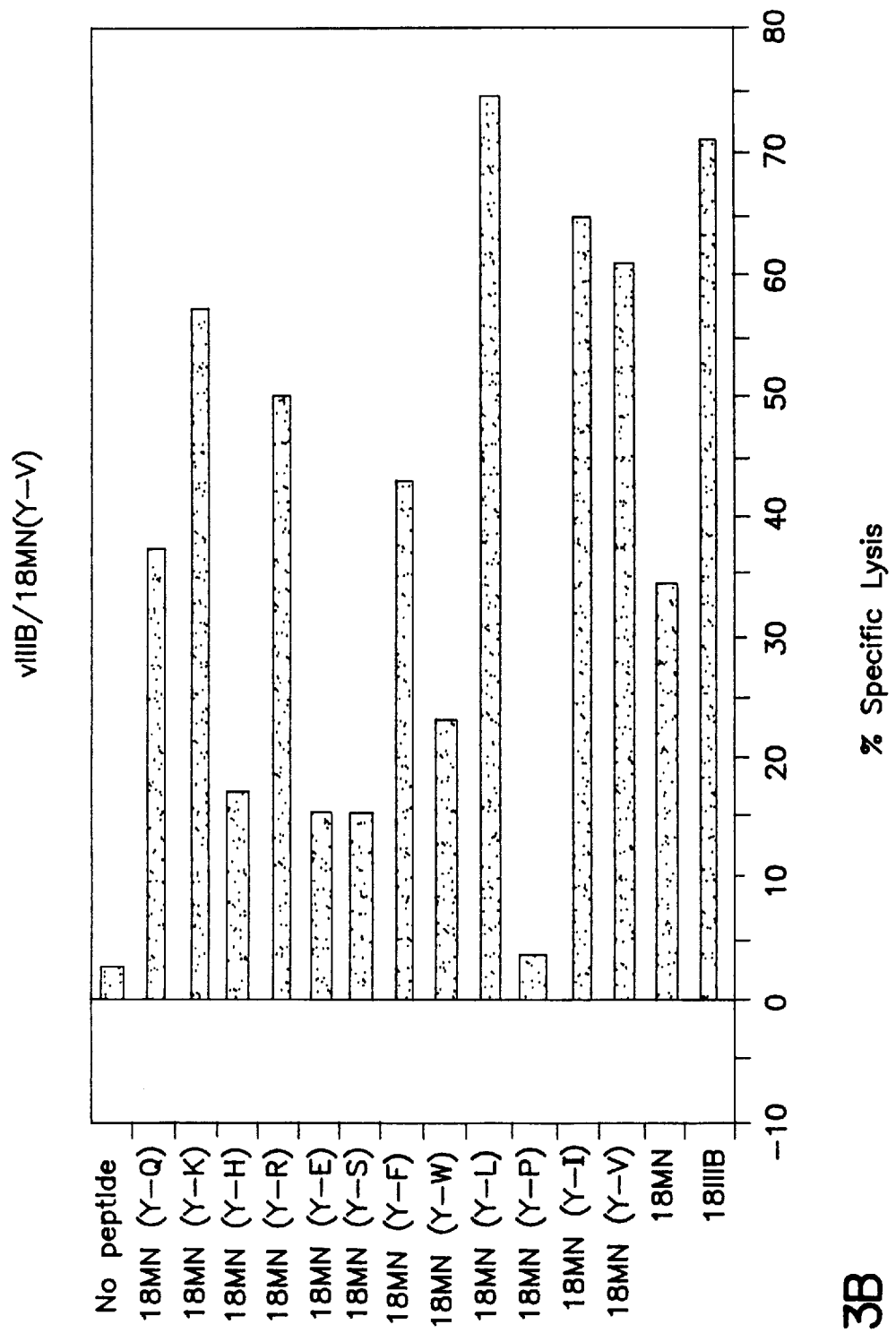
Figure 3C:
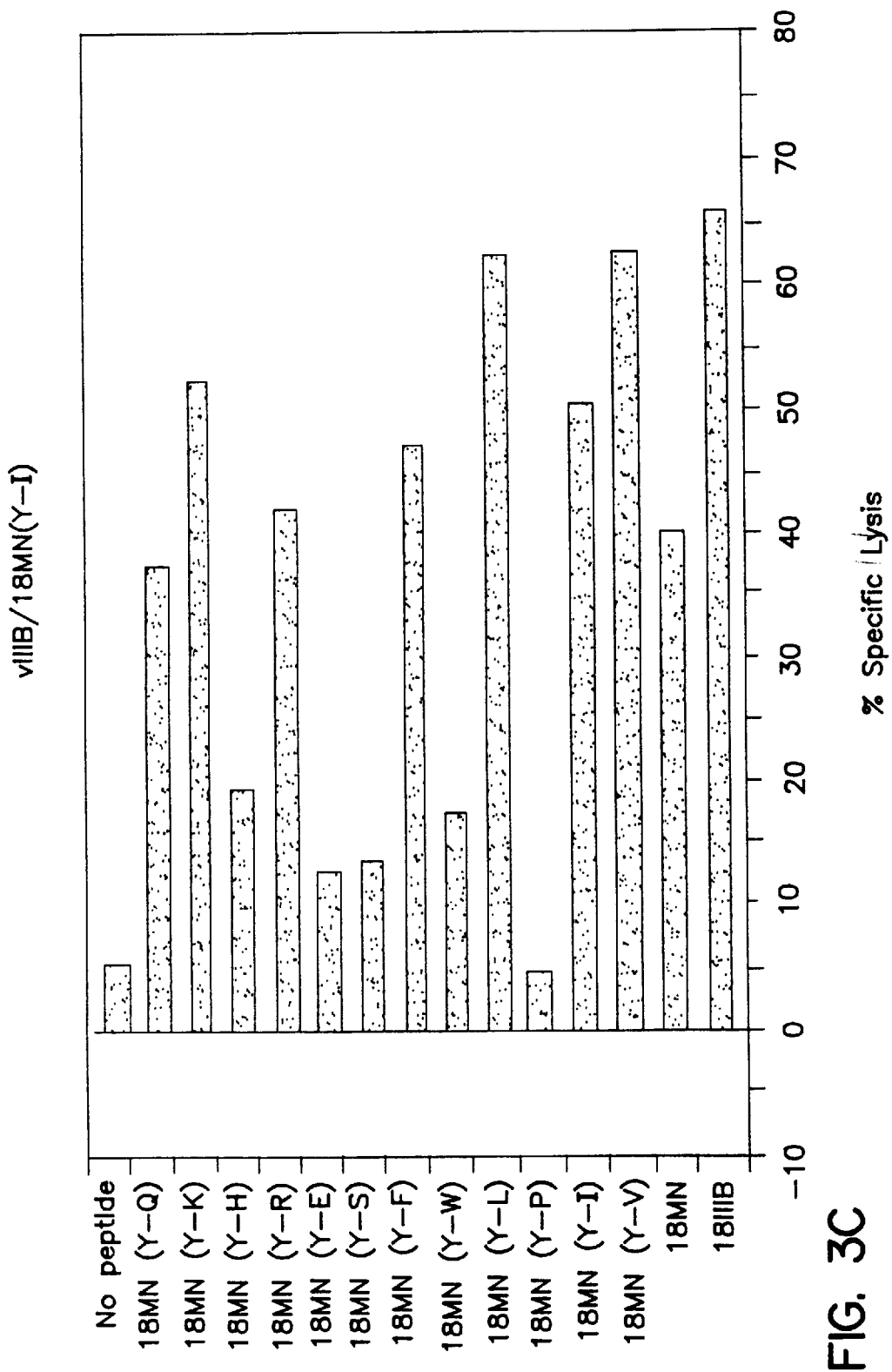
Figure 3D:
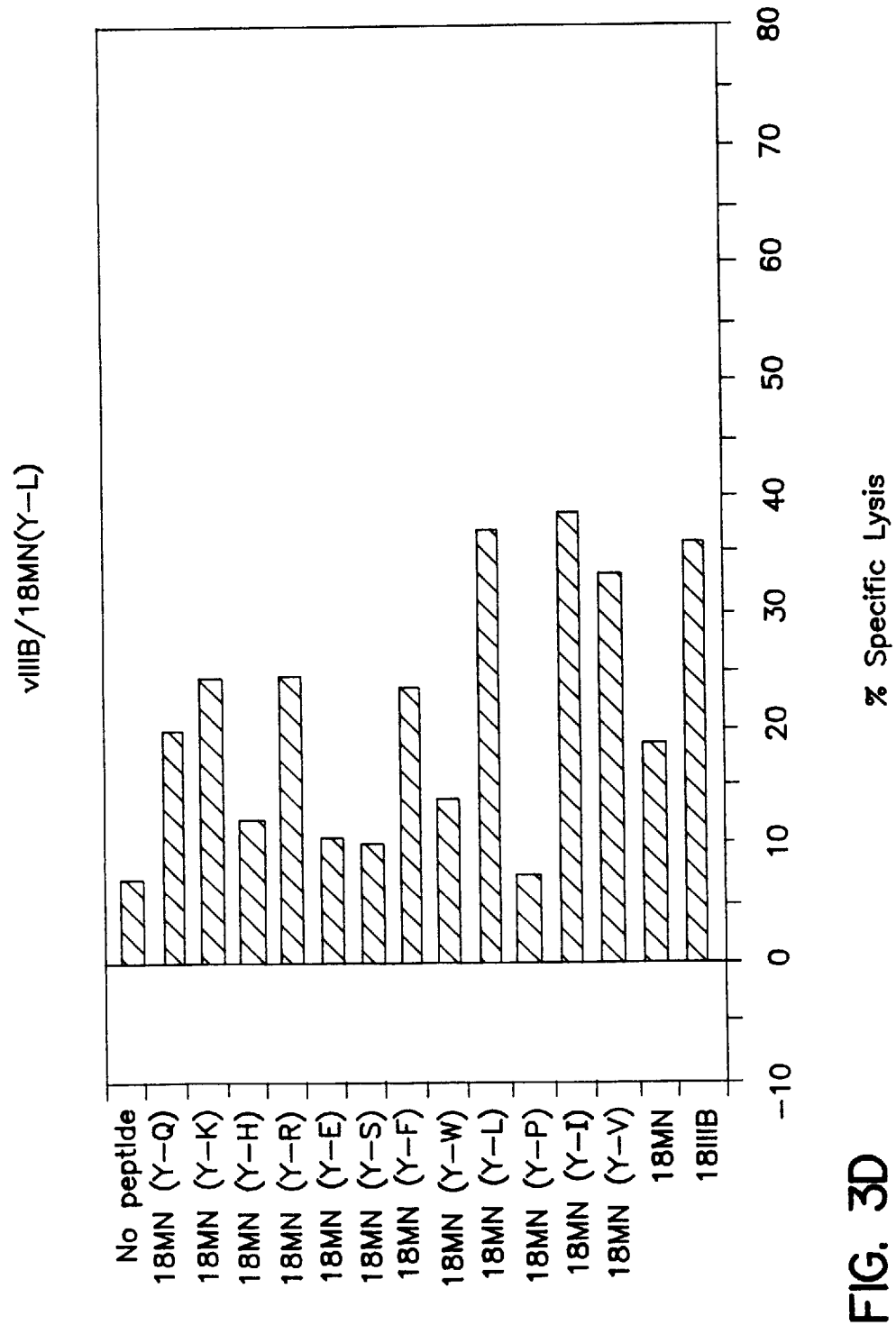
Figure 3E:
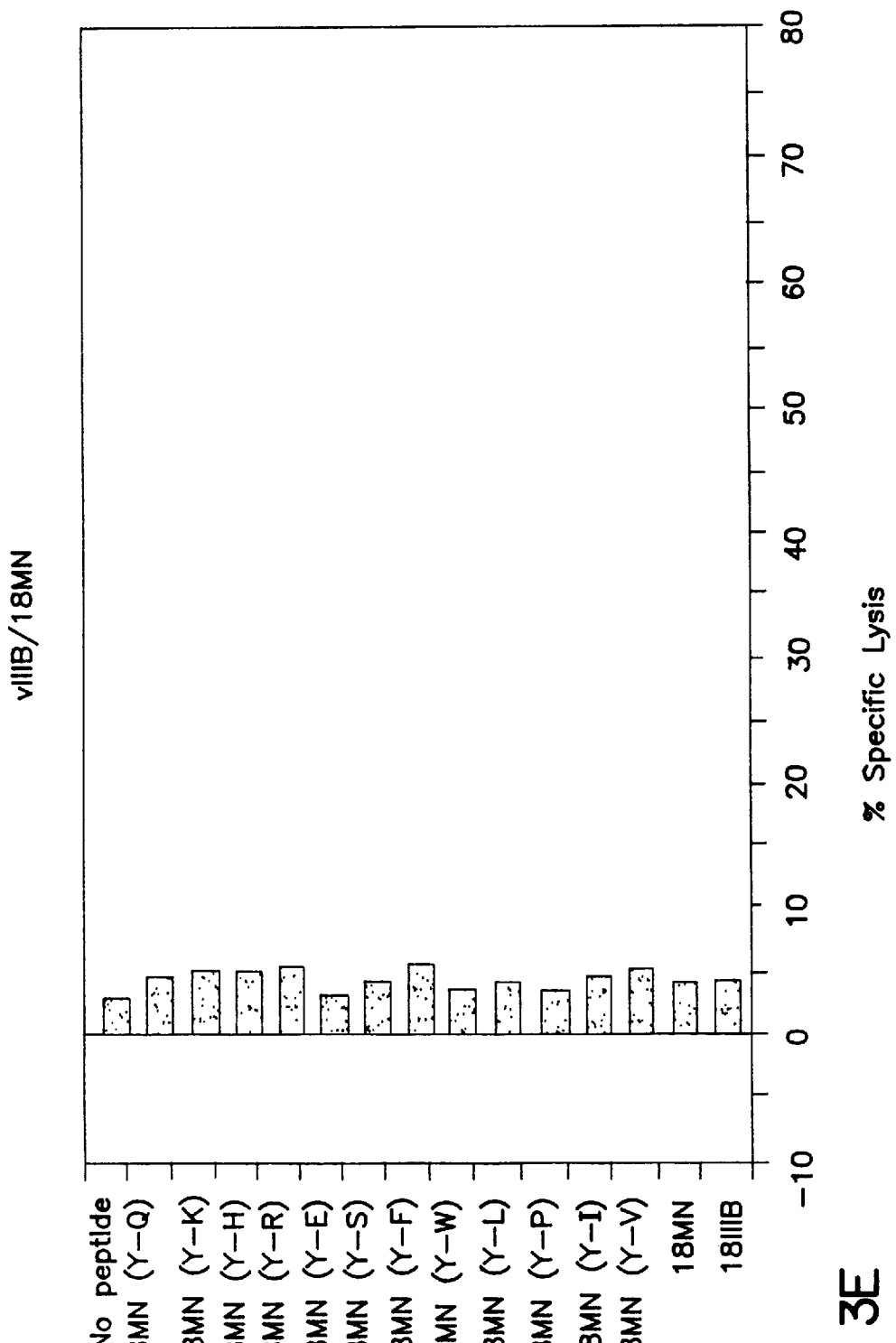
Figure 3F:
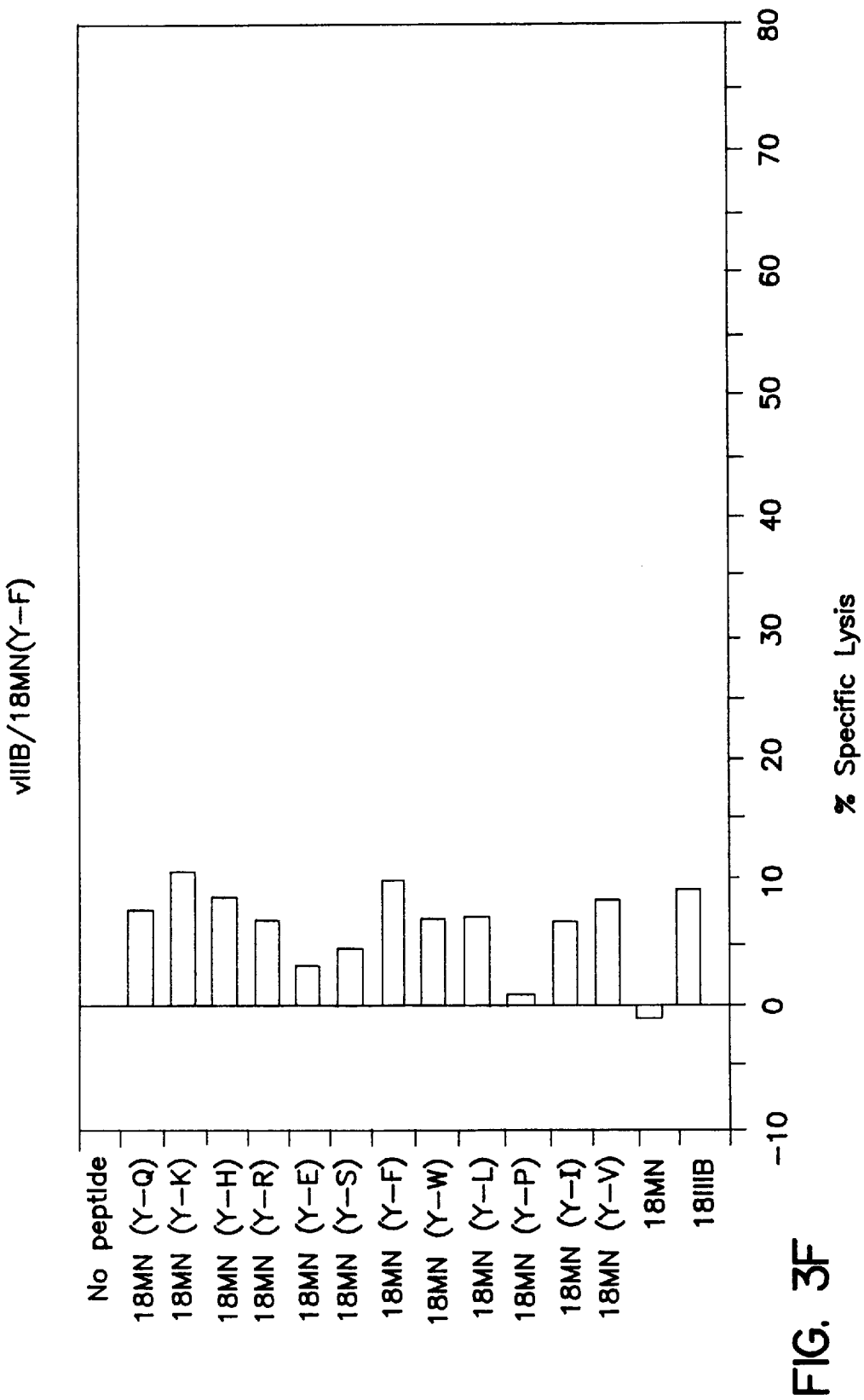
Figure 3G:
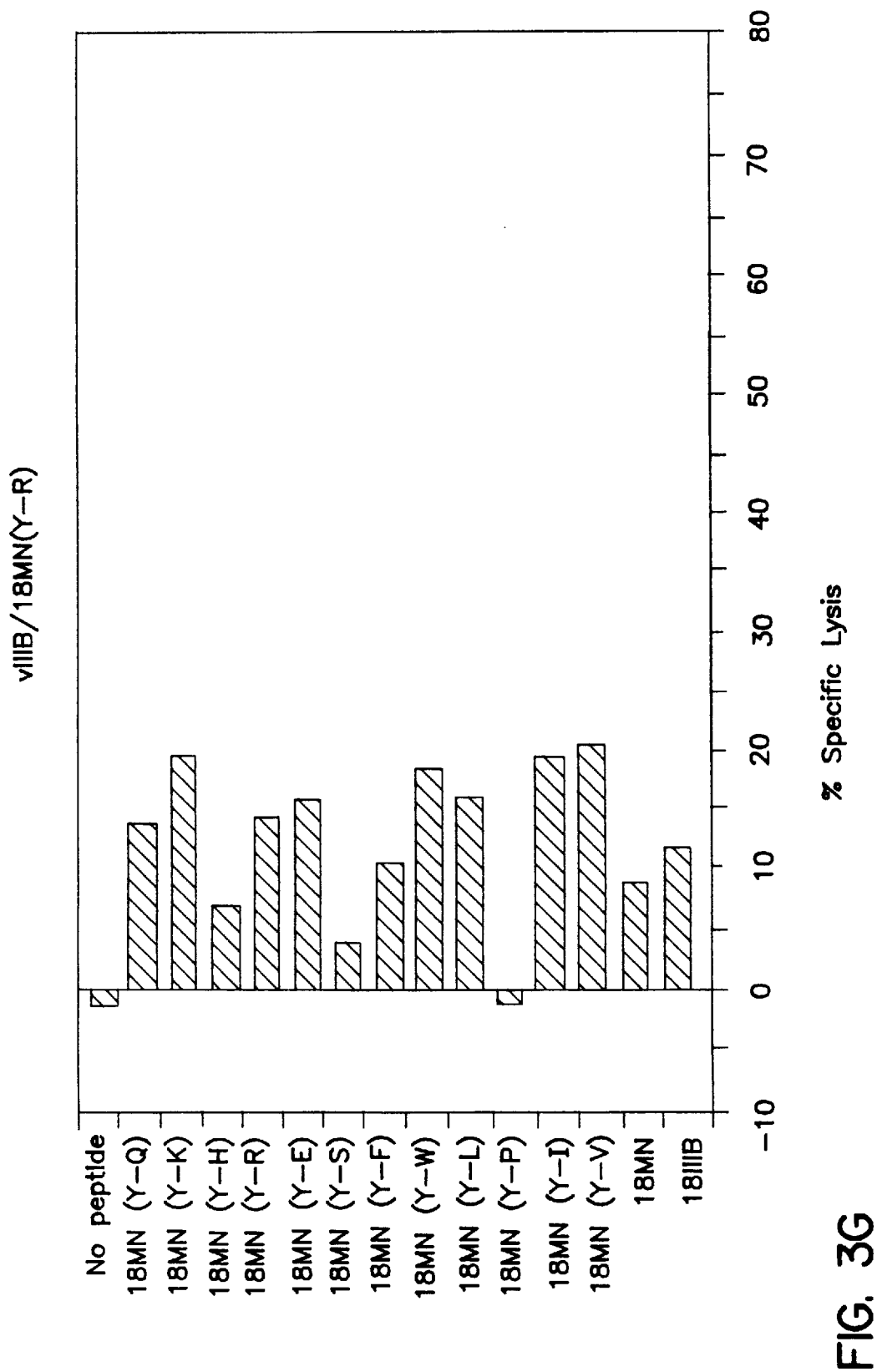
Figure 3H:
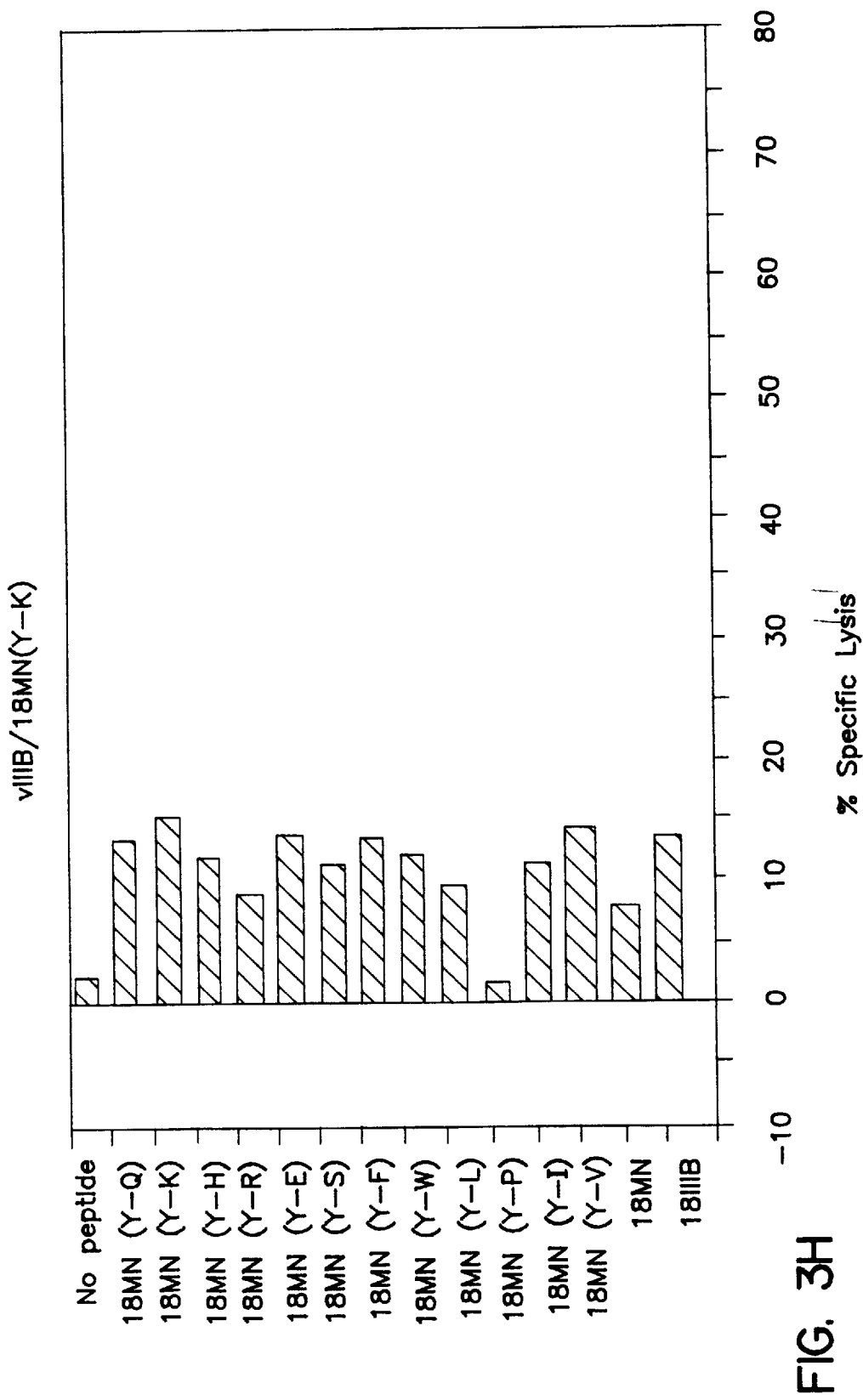

The pattern of CTL crossreactivity induced by restimulation with the original 18IIIB appears the same as that of the IIIB-specific CTL line (FIG. 3A). However, we find that we can generate CTL populations with significantly broader specificity when the IIIB-gp160 primed spleen cells are restimulated with 18 MN variant peptides containing aliphatic substitutions such as 18 MN(Y-V), 18 MN(Y-I), or 18 MN(Y-L) (FIG. 3B–D). Such CTL crossreactively lyse targets sensitized not only with the aliphatic substituted peptides themselves, but also targets exposed to 18 MN(Y-F), 18 MN(Y-R), 18 MN(Y-K), and, more weakly, to 18 MN, 18 MN(Y-W), 18 MN(Y-Q). Despite the cross-reactive killing by such effectors of targets sensitized with 18 MN and 18 MN-related peptides with aromatic or basic residues at 325, restimulation of IIIB-gp160 primed spleen cells with 18 MN itself (325 Y) (FIG. 3E) or 18 MN substituted peptides containing such aromatic or basic substitutions (FIG. 3F–H) does not induce any crossreactivity or indeed much specific CTL activity. The increased breadth of cross-reactivity elicited by the procedure of priming with gp160 IIIB-expressing vaccinia virus and boosting with 18 MN (Y-V) peptide is also apparent when the CTL are tested on natural HIV variant sequences. The CTL elicited by this procedure now lyse cells incubated with peptides corresponding to isolates RF, MN, SF2, and WMJ-2 (26%, 28%, 12%, and 7% specific lysis, respectively), whereas CTL raised only against the IIIB isolate do not (<1% lysis, see Table 1). They also lyse targets infected with recombinant vaccinia viruses vIIIB (vSC25) and vMN expressing the HIV-1IIIB and MN gp160 proteins endogenously, whereas CTL elicited by restimulation with the IIIB peptide only lysed targets infected with vIIIB.

These results show that enhanced cross-reactivity to a broad range of HIV-1 clinical isolates is attained by an immunization protocol which comprises a first immunization with a source of HIV-1 gp160 glycoprotein, followed by a second immunization with a synthetic chimeric peptide designed according to this invention. The chimeric polypeptide specifically consists of amino acid residues corresponding to residues 315–329 of the gp160 glycoprotein of HIV-1 strain IIIB from a first isolate or strain of HIV-1, except that the amino acid corresponding to residue 325 of IIIB is substituted with the homologous amino acid from a second isolate or strain. For example, in preferred embodiments of the invention, the chimeric polypeptide comprises the amino acids of the region homologous to 315–329 of strain IIIB that are obtained from strain MN, except that the tyrosine (Y) at the position homologous to 325 is substituted with valine (V), leucine (L) or isoleucine (I), designated herein as 18 MN(Y-V), 18 MN(Y-L) and 18 MN(Y-I), respectively. This substitution is made because V is the amino acid at position 325 in HIV-1, strain IIIB, while L and I are structurally similar to V in that all three are aliphatic amino acids.

The surprising result found according to the present invention is that the substitution of the position 325 amino acid from a second strain elicits cytotoxic T lymphocytes of increased cross-reactivity not just to that second strain, but to other strains as well. Thus a second presentation to the cellular immune system of the chimeric polypeptide according to the invention unexpectedly results in the production of cytotoxic T cells with an enhanced, broadened cross-reactivity to a broad range of HIV-1 isolates.

Example 4

Administration of recombinant vaccinia expressing gp160 and hybrid peptides as a vaccine against HIV-1

The aim of the research of a large number of biomedical researchers is the production of a vaccine which would produce protection to humans from infection by HIV-1 or therapeutic benefit in AIDS treatment. The instant invention provides peptides that may prove useful as candidates for such vaccines. A pharmaceutical composition including a vaccine in accordance with the present invention comprises an effective antigenic or therapeutic amount of at least one of the hybrid peptides and a pharmaceutically acceptable carrier such as physiological saline, non-toxic, sterile buffer and the like. Of course, additives such as preservatives, sterilants, adjuvants and the like, well known to one of ordinary skill in the art, could also be included in the pharmaceutical composition to maintain or increase the efficacy of the preparation.

It is proposed that peptides of the instant invention can be administered as part of a vaccination protocol in a fashion similar to that for the administration to primates of a synthetic peptide vaccine against hepatitis B as described by Itoh (Itoh, Y. et al., *Proc. Natl. Acad. Sci. USA* 83:9174–9178 (1986)). An alternative method for the preparation of vaccines involves the use of Protein A coated microbeads that bind immune complexes of an antibody and the immunizing antigen on their outer surface (Platt, et al., U.S. Pat. No. 4,493,825).

The administration of vaccinia virus as a vaccine is well-established art (Flexner, C. and Moss, B. in "New Generation Vaccines", pp. 189–206; G. C. Woodrow and M. M. Levine, eds. copyright 1990 by Marcel Dekker, New York, N.Y.). In the present invention, the recombinant vaccinia virus portion of the immunization protocol is performed by such established techniques.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A synthetic polypeptide having the amino acid sequence RIHIGPGRAFXTTKN, where X is selected from the group consisting of isoleucine, leucine, proline, tryptophan, phenylalanine, serine, glutamic acid, arginine, histidine, lysine and glutamine.

2. A synthetic polypeptide having the amino acid sequence RIHIGPGRAFXTTKN, where X is selected from the group consisting of isoleucine and leucine.

3. A peptide having an amino acid sequence selected from the group consisting of RIQRGPGRAFXTIGK, RIHIGPGRAFXTTKN, SITKGPGRVIXATGQ, SIHIGPGRAFXATGD, SLSIGPGRAFXTREI, SISIGPGRAFXATTD, SIYIGPGRAFXTTGR, GIAIGPGRTLXAREK, RVTLGPGRVWXTTGE, SIRIGPGKVFXAKGG, GIHFGPGQALXTTGI, STPIGLGQALXTTRG, STPIGLGQALXTTRI, and RTPTGLGQSLXTTRS, wherein X can be any amino acid, with the proviso that said peptide is not RIQRGPGRAFVTIGK, RIHIGPGRAFYTTKN, SITKGPGRVIYATGQ, SIHIGPGRAFYATGD, SLSIGPGRAFRTREI, SISIGPGRAFFATTD, SIYIGPGRAFHTTGR, GIAIGPGRTLYAREK, RVTLGPGRVWYTTGE, SIRIGPGKVFTAKGG, GIHFGPGQALYTTGI, STPIGLGQALYTTRG, STPIGLGQALYTTRI, RTPTGLGQSLYTTRS or RIHIGPGRAFVTTKN.

4. A peptide according to claim 3, wherein X is selected from the group consisting of glutamine, lysine, histidine, arginine, glutamic acid, serine, phenylalanine, tryptophan, leucine, proline, isoleucine and valine.

5. A peptide according to claim 3, wherein said amino acid sequence is selected from the group consisting of RIQRGPGRAFXTIGK, SLSIGPGRAFXTREI, SISIGPGRAFXATTD, SIYIGPGRAFHTTGR, and SIRIGPGKVFXAKGG, and wherein X is tyrosine.

6. A peptide according to claim 3, wherein said amino acid sequence is selected from the group consisting of RIHIGPGRAFXTTKN, SITKGPGRVIXATGQ, SIHIGPGRAFXATGD, GIAIGPGRTLXAREK, RVTLGPGRVWXTTGE, GIHFGPGQALXTTGI, STPIGLGQALXTTRG, STPIGLGQALXTTRI and RTPGLGQSLXTTRS, and wherein X is selected from the group consisting of valine, arginine, phenylalanine, histidine and threonine, with the proviso that said peptide is not RIHIGPGRAFVTTKN.

7. A peptide having an amino acid sequence selected from the group consisting of RIQRGPGRAFXTIGK, RIHIGPGRAFXTTKN, SITKGPGRVIXATGQ, SIHIGPGRAFXATGD, SLSIGPGRAFXTREI, SISIGPGRAFXATTD, SIYIGPGRAFXTTGR, GIAIGPGRTLXAREK, RVTLGPGRVWXTTGE, SIRIGPGKVFXAKGG, GIHFGPGQALXTTGI, STPIGLGQALXTTRG, STPIGLGQALXTTRI, and RTPTGLGQSLXTTRS, wherein X is selected from the group consisting of valine, tyrosine, arginine, phenylalanine, histidine and threonine, with the proviso that said peptide is not RIQRGPGRAFVTIGK, RIHIGPGRAFYTTKN, SITKGPGRVIYATGQ, SIHIGPGRAFYATGD, SLSIGPGRAFRTREI, SISIGPGRAFFATTD, SIYIGPGRAFHTTGR, GIAIGPGRTLYAREK, RVTLGPGRVWYTTGE, SIRIGPGKVFTAKGG, GIHFGPGQALYTTGI, STPIGLGQALYTTRG, STPIGLGQALYTTRI, RTPTGLGQSLYTTRS or RIHIGPGRAFVTTKN.

8. A peptide having the amino acid sequence SITKGPGRVIVATGQ or RIQRGPGRAFYTIGK.

* * * * *

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 15 amino acids (B) TYPE: amino acid
(D) TOPOLOGY: linear (ii) MOLECULE TYPE: peptide (v) FRAGMENT TYPE: internal (vi) ORIGINAL SOURCE:
    (A) ORGANISM: HIV-1
    (C) INDIVIDUAL ISOLATE: IIIB (ix) FEATURE:
    (A) NAME/KEY: Peptide
    (B) LOCATION: 1..15
    (D) OTHER INFORMATION: /label=peptide
        / note="synthetic peptide, sequence =residues 315
        to 329 of HIV-1, isolate IIIB, gp160 envelope
        glycoprotein."

(xi) SEQUENCE DESCRIPTION: SEQ ID NO:1:

```
Arg Ile Gln Arg Gly Pro Gly Arg Ala Phe Val Thr Ile Gly Lys
1               5                   10                  15
```

(2) INFORMATION FOR SEQ ID NO:2:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: HIV-1
        (C) INDIVIDUAL ISOLATE: MN (ix) FEATURE:
        (A) NAME/KEY: Peptide
        (B) LOCATION: 1..15
        (D) OTHER INFORMATION: /label=peptide
            / note="synthetic peptide, sequence =amino acids
            315 - 329 of HIV-1, isolate MN, gp160 envelope
            glycoprotein"

(ix) FEATURE:
        (A) NAME/KEY: Region
        (B) LOCATION: 11
        (D) OTHER INFORMATION: /label=substitution
            / note="substitution of V,I or L for Y at this
            position produces a "hybrid"peptide that elicits
            CTL specific for a broad range of HIV-1 isolates (xi) SEQUENCE DESCRIPTION: SEQ ID NO:2:

```
Arg Ile His Ile Gly Pro Gly Arg Ala Phe Tyr Thr Thr Lys Asn
1               5                   10                  15
```

(2) INFORMATION FOR SEQ ID NO:3:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: HIV-1
        (C) INDIVIDUAL ISOLATE: RF (ix) FEATURE:
        (A) NAME/KEY: Peptide
        (B) LOCATION: 1..15

( D ) OTHER INFORMATION: /label=peptide
/ note="synthetic peptide, sequence =amino acids
315 - 329 of HIV-1, isolate RF, gp160 envelope
glycoprotein"

( x i ) SEQUENCE DESCRIPTION: SEQ ID NO:3:

Ser Ile Thr Lys Gly Pro Gly Arg Val Ile Tyr Ala Thr Gly Gln
1               5                   10                  15

( 2 ) INFORMATION FOR SEQ ID NO:4:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: HIV-1
        ( C ) INDIVIDUAL ISOLATE: SC ( i x ) FEATURE:
        ( A ) NAME/KEY: Peptide
        ( B ) LOCATION: 1..15
        ( D ) OTHER INFORMATION: /label=peptide
/ note="synthetic peptide, sequence =amino acids
315 - 329 of HIV-1, isolate SC, gp160 envelope
glycoprotein"

( x i ) SEQUENCE DESCRIPTION: SEQ ID NO:4:

Ser Ile His Ile Gly Pro Gly Arg Ala Phe Tyr Ala Thr Gly Asp
1               5                   10                  15

( 2 ) INFORMATION FOR SEQ ID NO:5:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: HIV-1
        ( C ) INDIVIDUAL ISOLATE: WJM-2

( i x ) FEATURE:
        ( A ) NAME/KEY: Peptide
        ( B ) LOCATION: 1..15
        ( D ) OTHER INFORMATION: /label=peptide
/ note="synthetic peptide, sequence =amino acids
315 - 329 of HIV-1, isolate WMJ-2, gp160 envelope
glycoprotein"

( x i ) SEQUENCE DESCRIPTION: SEQ ID NO:5:

Ser Leu Ser Ile Gly Pro Gly Arg Ala Phe Arg Thr Arg Glu Ile
1               5                   10                  15

( 2 ) INFORMATION FOR SEQ ID NO:6:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( v ) FRAGMENT TYPE: internal (v i) ORIGINAL SOURCE:
    (A) ORGANISM: HIV-1
    (C) INDIVIDUAL ISOLATE: Z321

(i x) FEATURE:
    (A) NAME/KEY: Peptide
    (B) LOCATION: 1..15
    (D) OTHER INFORMATION: /label=peptide
        / note="synthetic peptide, sequence =amino acids
        315 - 329 of HIV-1, isolate Z321, gp160 envelope
        glycoprotein"

(x i) SEQUENCE DESCRIPTION: SEQ ID NO:6:

```
Ser  Ile  Ser  Ile  Gly  Pro  Gly  Arg  Ala  Phe  Phe  Ala  Thr  Thr  Asp
1                   5                        10                       15
```

(2) INFORMATION FOR SEQ ID NO:7:

(i) SEQUENCE CHARACTERISTICS:
    (A) LENGTH: 15 amino acids
    (B) TYPE: amino acid
    (D) TOPOLOGY: linear (i i) MOLECULE TYPE: peptide (v) FRAGMENT TYPE: internal (v i) ORIGINAL SOURCE:
    (A) ORGANISM: HIV-1
    (C) INDIVIDUAL ISOLATE: SF2

(i x) FEATURE:
    (A) NAME/KEY: Peptide
    (B) LOCATION: 1..15
    (D) OTHER INFORMATION: /label=peptide
        / note="synthetic peptide, sequence =amino acids
        315 - 329 of HIV-1, isolate SF2, gp160 envelope
        glycoprotein"

(x i) SEQUENCE DESCRIPTION: SEQ ID NO:7:

```
Ser  Ile  Tyr  Ile  Gly  Pro  Gly  Arg  Ala  Phe  His  Thr  Thr  Gly  Arg
1                   5                        10                       15
```

(2) INFORMATION FOR SEQ ID NO:8:

(i) SEQUENCE CHARACTERISTICS:
    (A) LENGTH: 15 amino acids
    (B) TYPE: amino acid
    (D) TOPOLOGY: linear (i i) MOLECULE TYPE: peptide (v) FRAGMENT TYPE: internal (v i) ORIGINAL SOURCE:
    (A) ORGANISM: HIV-1
    (C) INDIVIDUAL ISOLATE: NY5

(i x) FEATURE:
    (A) NAME/KEY: Peptide
    (B) LOCATION: 1..15
    (D) OTHER INFORMATION: /label=peptide
        / note="synthetic peptide, sequence =amino acids
        315 - 329 of HIV-1, isolate NY5, gp160 envelope
        glycoprotein"

(x i) SEQUENCE DESCRIPTION: SEQ ID NO:8:

```
Gly  Ile  Ala  Ile  Gly  Pro  Gly  Arg  Thr  Leu  Tyr  Ala  Arg  Glu  Lys
1                   5                        10                       15
```

(2) INFORMATION FOR SEQ ID NO:9:

(i) SEQUENCE CHARACTERISTICS:
    (A) LENGTH: 15 amino acids ( B ) TYPE: amino acid
             ( D ) TOPOLOGY: linear ( i i ) MOLECULE TYPE: peptide ( v ) FRAGMENT TYPE: internal ( v i ) ORIGINAL SOURCE:
             ( A ) ORGANISM: HIV-1
             ( C ) INDIVIDUAL ISOLATE: CDC4

( i x ) FEATURE:
             ( A ) NAME/KEY: Peptide
             ( B ) LOCATION: 1..15
             ( D ) OTHER INFORMATION: /label=peptide
                      / note="synthetic peptide, sequence =amino acids
                      315 - 329 of HIV-1, isolate CDC4, gp160 envelope
                      glycoprotein"

( x i ) SEQUENCE DESCRIPTION: SEQ ID NO:9:

Arg  Val  Thr  Leu  Gly  Pro  Gly  Arg  Val  Trp  Tyr  Thr  Thr  Gly  Glu
1              5                        10                       15

( 2 ) INFORMATION FOR SEQ ID NO:10:

( i ) SEQUENCE CHARACTERISTICS:
             ( A ) LENGTH: 15 amino acids
             ( B ) TYPE: amino acid
             ( D ) TOPOLOGY: linear ( i i ) MOLECULE TYPE: peptide ( v ) FRAGMENT TYPE: internal ( v i ) ORIGINAL SOURCE:
             ( A ) ORGANISM: HIV-1
             ( C ) INDIVIDUAL ISOLATE: Z3

( i x ) FEATURE:
             ( A ) NAME/KEY: Peptide
             ( B ) LOCATION: 1..15
             ( D ) OTHER INFORMATION: /label=peptide
                      / note="synthetic peptide, sequence =amino acids
                      315 - 329 of HIV-1, isolate Z3, gp160 envelope
                      glycoprotein"

( x i ) SEQUENCE DESCRIPTION: SEQ ID NO:10:

Ser  Ile  Arg  Ile  Gly  Pro  Gly  Lys  Val  Phe  Thr  Ala  Lys  Gly  Gly
1              5                        10                       15

( 2 ) INFORMATION FOR SEQ ID NO:11:

( i ) SEQUENCE CHARACTERISTICS:
             ( A ) LENGTH: 15 amino acids
             ( B ) TYPE: amino acid
             ( D ) TOPOLOGY: linear ( i i ) MOLECULE TYPE: peptide ( v ) FRAGMENT TYPE: internal ( v i ) ORIGINAL SOURCE:
             ( A ) ORGANISM: HIV-1
             ( C ) INDIVIDUAL ISOLATE: MAL ( i x ) FEATURE:
             ( A ) NAME/KEY: Peptide
             ( B ) LOCATION: 1..15
             ( D ) OTHER INFORMATION: /label=peptide
                      / note="synthetic peptide, sequence =amino acids
                      315 - 329 of HIV-1, isolate MAL, gp160 envelope
                      glycoprotein"

( x i ) SEQUENCE DESCRIPTION: SEQ ID NO:11:

Gly  Ile  His  Phe  Gly  Pro  Gly  Gln  Ala  Leu  Tyr  Thr  Thr  Gly  Ile

```
                1               5                      1 0                    1 5
```

( 2 ) INFORMATION FOR SEQ ID NO:12:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( v ) FRAGMENT TYPE: internal ( v i ) ORIGINAL SOURCE:
    ( A ) ORGANISM: HIV-1
    ( C ) INDIVIDUAL ISOLATE: Z6

( i x ) FEATURE:
    ( A ) NAME/KEY: Peptide
    ( B ) LOCATION: 1..15
    ( D ) OTHER INFORMATION: /label=peptide
        / note="synthetic peptide, sequence =amino acids
        315 - 329 of HIV-1, isolate Z6, gp160 envelope
        glycoprotein"

( x i ) SEQUENCE DESCRIPTION: SEQ ID NO:12:

```
Ser  Thr  Pro  Ile  Gly  Leu  Gly  Gln  Ala  Leu  Tyr  Thr  Thr  Arg  Gly
1                  5                      1 0                    1 5
```

( 2 ) INFORMATION FOR SEQ ID NO:13:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( v ) FRAGMENT TYPE: internal ( v i ) ORIGINAL SOURCE:
    ( A ) ORGANISM: HIV-1
    ( C ) INDIVIDUAL ISOLATE: JY1

( i x ) FEATURE:
    ( A ) NAME/KEY: Peptide
    ( B ) LOCATION: 1..15
    ( D ) OTHER INFORMATION: /label=peptide
        / note="synthetic peptide, sequence =amino acids
        315 - 329 of HIV-1, isolate JY1, gp160 envelope
        glycoprotein"

( x i ) SEQUENCE DESCRIPTION: SEQ ID NO:13:

```
Ser  Thr  Pro  Ile  Gly  Leu  Gly  Gln  Ala  Leu  Tyr  Thr  Thr  Arg  Ile
1                  5                      1 0                    1 5
```

( 2 ) INFORMATION FOR SEQ ID NO:14:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( v ) FRAGMENT TYPE: internal ( v i ) ORIGINAL SOURCE:
    ( A ) ORGANISM: HIV-1
    ( C ) INDIVIDUAL ISOLATE: ELI ( i x ) FEATURE:
    ( A ) NAME/KEY: Peptide
    ( B ) LOCATION: 1..15
    ( D ) OTHER INFORMATION: /label=peptide / note="synthetic peptide, sequence =amino acids
315 - 329 of HIV-1, isolate ELI, gp160 envelope
glycoprotein"

( x i ) SEQUENCE DESCRIPTION: SEQ ID NO:14:

| Arg | Thr | Pro | Thr | Gly | Leu | Gly | Gln | Ser | Leu | Tyr | Thr | Thr | Arg | Ser |
|---|---|---|---|---|---|---|---|---|---|---|---|---|---|---|
| 1 | | | | 5 | | | | | 10 | | | | | 15 |

( 2 ) INFORMATION FOR SEQ ID NO:15:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: HIV-1

( i x ) FEATURE:
        ( A ) NAME/KEY: Peptide
        ( B ) LOCATION: 1..15
        ( D ) OTHER INFORMATION: /label=peptide
            / note="peptide 18MN(Y-Q); synthetic, chimeric
            peptide; sequence =region of HIV-1 strain MN
            gp160 envelope glycoprotein that is homologous to ( x i ) SEQUENCE DESCRIPTION: SEQ ID NO:15:

| Arg | Ile | His | Ile | Gly | Pro | Gly | Arg | Ala | Phe | Gln | Thr | Thr | Lys | Asn |
|---|---|---|---|---|---|---|---|---|---|---|---|---|---|---|
| 1 | | | | 5 | | | | | 10 | | | | | 15 |

( 2 ) INFORMATION FOR SEQ ID NO:16:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: HIV-1

( i x ) FEATURE:
        ( A ) NAME/KEY: Peptide
        ( B ) LOCATION: 1..15
        ( D ) OTHER INFORMATION: /label=peptide
            / note="peptide 18MN(Y-V); synthetic, chimeric
            peptide; sequence =region of HIV-1 strain MN
            gp160 envelope glycoprotein that is homologous to ( x i ) SEQUENCE DESCRIPTION: SEQ ID NO:16:

| Arg | Ile | His | Ile | Gly | Pro | Gly | Arg | Ala | Phe | Val | Thr | Thr | Lys | Asn |
|---|---|---|---|---|---|---|---|---|---|---|---|---|---|---|
| 1 | | | | 5 | | | | | 10 | | | | | 15 |

( 2 ) INFORMATION FOR SEQ ID NO:17:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: HIV-1

( i x ) FEATURE:
    ( A ) NAME/KEY: Peptide
    ( B ) LOCATION: 1..15
    ( D ) OTHER INFORMATION: /label=peptide
        / note="peptide 18MN(Y-I); synthetic, chimeric
        peptide; sequence =region of HIV-1 strain MN
        gp160 envelope glycoprotein that is homologous to ( x i ) SEQUENCE DESCRIPTION: SEQ ID NO:17:

```
Arg  Ile  His  Ile  Gly  Pro  Gly  Arg  Ala  Phe  Ile  Thr  Thr  Lys  Asn
1                   5                        10                       15
```

( 2 ) INFORMATION FOR SEQ ID NO:18:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: HIV-1

( i x ) FEATURE:
        ( A ) NAME/KEY: Peptide
        ( B ) LOCATION: 1..15
        ( D ) OTHER INFORMATION: /label=peptide
            / note="peptide 18MN(Y-P); synthetic, chimeric
            peptide; sequence =region of HIV-1 strain MN
            gp160 envelope glycoprotein that is homologous to ( x i ) SEQUENCE DESCRIPTION: SEQ ID NO:18:

```
Arg  Ile  His  Ile  Gly  Pro  Gly  Arg  Ala  Phe  Pro  Thr  Thr  Lys  Asn
1                   5                        10                       15
```

( 2 ) INFORMATION FOR SEQ ID NO:19:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: HIV-1

( i x ) FEATURE:
        ( A ) NAME/KEY: Peptide
        ( B ) LOCATION: 1..15
        ( D ) OTHER INFORMATION: /label=peptide
            / note="peptide 18MN(Y-L); synthetic, chimeric
            peptide; sequence =region of HIV-1 strain MN
            gp160 envelope glycoprotein that is homologous to ( x i ) SEQUENCE DESCRIPTION: SEQ ID NO:19:

```
Arg  Ile  His  Ile  Gly  Pro  Gly  Arg  Ala  Phe  Leu  Thr  Thr  Lys  Asn
1                   5                        10                       15
```

( 2 ) INFORMATION FOR SEQ ID NO:20:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
            ( A ) ORGANISM: HIV-1

( i x ) FEATURE:
            ( A ) NAME/KEY: Peptide
            ( B ) LOCATION: 1..15
            ( D ) OTHER INFORMATION: /label=peptide
                        / note="peptide 18MN(Y-W); synthetic, chimeric
                        peptide; sequence =region of HIV-1 strain MN
                        gp160 envelope glycoprotein that is homologous to ( x i ) SEQUENCE DESCRIPTION: SEQ ID NO:20:

Arg  Ile  His  Ile  Gly  Pro  Gly  Arg  Ala  Phe  Trp  Thr  Thr  Lys  Asn
1                  5                            10                           15

( 2 ) INFORMATION FOR SEQ ID NO:21:

( i ) SEQUENCE CHARACTERISTICS:
            ( A ) LENGTH: 15 amino acids
            ( B ) TYPE: amino acid
            ( D ) TOPOLOGY: linear ( i i ) MOLECULE TYPE: peptide ( v ) FRAGMENT TYPE: internal ( v i ) ORIGINAL SOURCE:
            ( A ) ORGANISM: HIV-1

( i x ) FEATURE:
            ( A ) NAME/KEY: Peptide
            ( B ) LOCATION: 1..15
            ( D ) OTHER INFORMATION: /label=peptide
                        / note="peptide 18MN(Y-F); synthetic, chimeric
                        peptide; sequence =region of HIV-1 strain MN
                        gp160 envelope glycoprotein that is homologous to ( x i ) SEQUENCE DESCRIPTION: SEQ ID NO:21:

Arg  Ile  His  Ile  Gly  Pro  Gly  Arg  Ala  Phe  Phe  Thr  Thr  Lys  Asn
1                  5                            10                           15

( 2 ) INFORMATION FOR SEQ ID NO:22:

( i ) SEQUENCE CHARACTERISTICS:
            ( A ) LENGTH: 15 amino acids
            ( B ) TYPE: amino acid
            ( D ) TOPOLOGY: linear ( i i ) MOLECULE TYPE: peptide ( v ) FRAGMENT TYPE: internal ( v i ) ORIGINAL SOURCE:
            ( A ) ORGANISM: HIV-1

( i x ) FEATURE:
            ( A ) NAME/KEY: Peptide
            ( B ) LOCATION: 1..15
            ( D ) OTHER INFORMATION: /label=peptide
                        / note="peptide 18MN(Y-S); synthetic, chimeric
                        peptide; sequence =region of HIV-1 strain MN
                        gp160 envelope glycoprotein that is homologous to ( x i ) SEQUENCE DESCRIPTION: SEQ ID NO:22:

Arg  Ile  His  Ile  Gly  Pro  Gly  Arg  Ala  Phe  Ser  Thr  Thr  Lys  Asn
1                  5                            10                           15

( 2 ) INFORMATION FOR SEQ ID NO:23:

( i ) SEQUENCE CHARACTERISTICS:
            ( A ) LENGTH: 15 amino acids
            ( B ) TYPE: amino acid
            ( D ) TOPOLOGY: linear ( i i ) MOLECULE TYPE: peptide ( v ) FRAGMENT TYPE: internal ( v i ) ORIGINAL SOURCE:
    ( A ) ORGANISM: HIV-1

( i x ) FEATURE:
    ( A ) NAME/KEY: Peptide
    ( B ) LOCATION: 1..15
    ( D ) OTHER INFORMATION: /label=peptide
    / note="peptide 18MN(Y-E); synthetic, chimeric peptide; sequence =region of HIV-1 strain MN gp160 envelope glycoprotein that is homologous to ( x i ) SEQUENCE DESCRIPTION: SEQ ID NO:23:

```
Arg  Ile  His  Ile  Gly  Pro  Gly  Arg  Ala  Phe  Glu  Thr  Thr  Lys  Asn
1                  5                       10                         15
```

( 2 ) INFORMATION FOR SEQ ID NO:24:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( v ) FRAGMENT TYPE: internal ( v i ) ORIGINAL SOURCE:
    ( A ) ORGANISM: HIV-1

( i x ) FEATURE:
    ( A ) NAME/KEY: Peptide
    ( B ) LOCATION: 1..15
    ( D ) OTHER INFORMATION: /label=peptide
    / note="peptide 18MN(Y-R); synthetic, chimeric peptide; sequence =region of HIV-1 strain MN gp160 envelope glycoprotein that is homologous to ( x i ) SEQUENCE DESCRIPTION: SEQ ID NO:24:

```
Arg  Ile  His  Ile  Gly  Pro  Gly  Arg  Ala  Phe  Arg  Thr  Thr  Lys  Asn
1                  5                       10                         15
```

( 2 ) INFORMATION FOR SEQ ID NO:25:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( v ) FRAGMENT TYPE: internal ( v i ) ORIGINAL SOURCE:
    ( A ) ORGANISM: HIV-1

( i x ) FEATURE:
    ( A ) NAME/KEY: Peptide
    ( B ) LOCATION: 1..15
    ( D ) OTHER INFORMATION: /label=peptide
    / note="peptide 18MN(Y-H); synthetic, chimeric peptide; sequence =region of HIV-1 strain MN gp160 envelope glycoprotein that is homologous to ( x i ) SEQUENCE DESCRIPTION: SEQ ID NO:25:

```
Arg  Ile  His  Ile  Gly  Pro  Gly  Arg  Ala  Phe  His  Thr  Thr  Lys  Asn
1                  5                       10                         15
```

( 2 ) INFORMATION FOR SEQ ID NO:26:

(i) SEQUENCE CHARACTERISTICS:
  (A) LENGTH: 15 amino acids
  (B) TYPE: amino acid
  (D) TOPOLOGY: linear (ii) MOLECULE TYPE: peptide (v) FRAGMENT TYPE: internal (vi) ORIGINAL SOURCE:
  (A) ORGANISM: HIV-1

(ix) FEATURE:
  (A) NAME/KEY: Peptide
  (B) LOCATION: 1..15
  (D) OTHER INFORMATION: /label=peptide
    / note="peptide 18MN(Y-K); synthetic, chimeric
    peptide; sequence =region of HIV-1 strain MN
    gp160 envelope glycoprotein that is homologous to (xi) SEQUENCE DESCRIPTION: SEQ ID NO:26:

Arg Ile His Ile Gly Pro Gly Arg Ala Phe Lys Thr Thr Lys Asn
1               5                   10                  15